US010488375B2

(12) United States Patent
Auner et al.

(10) Patent No.: US 10,488,375 B2
(45) Date of Patent: Nov. 26, 2019

(54) SYSTEM FOR DETECTING LIQUID ANALYTES

(71) Applicant: Venica Fluid Sciences Limited, Road Town, Tortola (VG)

(72) Inventors: Gregory W. Auner, Livonia, MI (US); Michelle A. Brusatori, Sterling Heights, MI (US); Ronald F. Johnson, Whittier, CA (US)

(73) Assignee: Venica Fluid Sciences Limited, Road Town, Tortola (VG)

( * ) Notice: Subject to any disclaimer, the term of this patent is extended or adjusted under 35 U.S.C. 154(b) by 0 days.

(21) Appl. No.: 15/994,737

(22) Filed: May 31, 2018

(65) Prior Publication Data
US 2018/0348175 A1 Dec. 6, 2018

Related U.S. Application Data

(60) Provisional application No. 62/514,375, filed on Jun. 2, 2017.

(51) Int. Cl.
| G01N 30/60 | (2006.01) |
| G01N 30/38 | (2006.01) |
| G01N 30/02 | (2006.01) |
| G01N 30/74 | (2006.01) |

(52) U.S. Cl.
CPC ......... *G01N 30/6095* (2013.01); *G01N 30/38* (2013.01); *G01N 30/6091* (2013.01); *G01N 30/6069* (2013.01); *G01N 30/74* (2013.01); *G01N 2030/027* (2013.01)

(58) Field of Classification Search
CPC .... G01N 30/26; G01N 30/38; G01N 30/6091; G01N 30/6095; G01N 2030/528
See application file for complete search history.

(56) References Cited

U.S. PATENT DOCUMENTS

| 7,178,386 | B1* | 2/2007 | Gamble | G01N 30/466 |
| | | | | 210/198.2 |
| 7,217,367 | B2* | 5/2007 | Huang | G01N 30/6095 |
| | | | | 137/625.46 |
| 8,702,976 | B2* | 4/2014 | Peterman | B01L 3/502761 |
| | | | | 210/142 |
| 2002/0137218 | A1* | 9/2002 | Mian | B29C 59/14 |
| | | | | 436/45 |
| 2002/0176804 | A1* | 11/2002 | Strand | B01J 19/0093 |
| | | | | 422/400 |
| 2002/0185183 | A1* | 12/2002 | O'Connor | B01F 5/064 |
| | | | | 137/814 |
| 2002/0187557 | A1* | 12/2002 | Hobbs | G01N 30/16 |
| | | | | 436/161 |
| 2004/0217279 | A1* | 11/2004 | Hobbs | G01N 30/6043 |
| | | | | 250/288 |
| 2010/0059414 | A1* | 3/2010 | Sturm | G01N 27/44791 |
| | | | | 209/155 |

(Continued)

FOREIGN PATENT DOCUMENTS

WO WO-2014065861 A1 * 5/2014 .......... C12Q 1/6897

*Primary Examiner* — Nathaniel J Kolb
(74) *Attorney, Agent, or Firm* — Bejin Bieneman PLC

(57) ABSTRACT

A sample cartridge for a liquid chromatography device includes a microfluidic chip. A collector in the microfluidic chip includes a collector flow channel and a first window for acquisition of spectral data from a sample in the collector flow channel.

16 Claims, 16 Drawing Sheets

(56) References Cited

U.S. PATENT DOCUMENTS

| | | | |
|---|---|---|---|
| 2010/0155243 A1* | 6/2010 | Schneider | G01N 33/558 204/452 |
| 2010/0173398 A1* | 7/2010 | Peterman | B01L 3/502761 435/288.7 |
| 2012/0252129 A1* | 10/2012 | Fu | G01N 1/2202 436/128 |
| 2014/0030732 A1 | 1/2014 | Staples | |
| 2016/0067634 A1* | 3/2016 | Richardson | B01L 9/527 210/488 |
| 2018/0059005 A1* | 3/2018 | Marshall | G01N 21/1717 |

\* cited by examiner

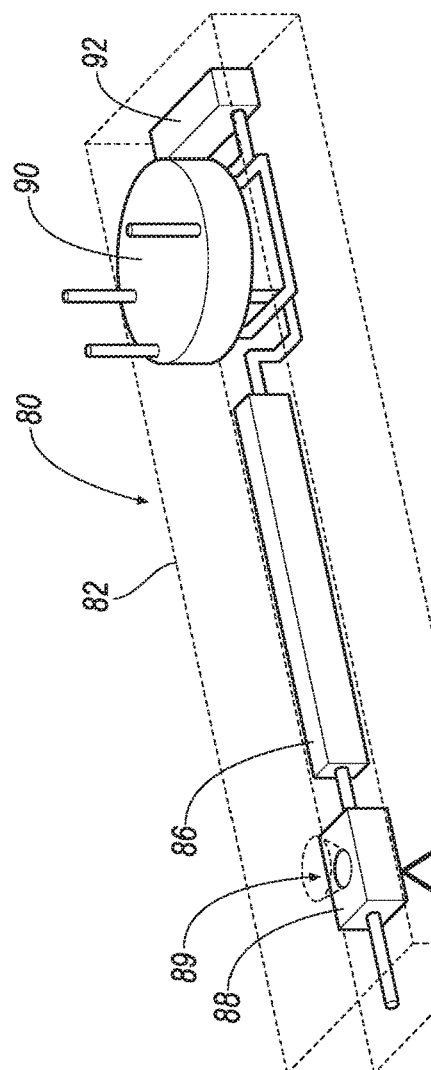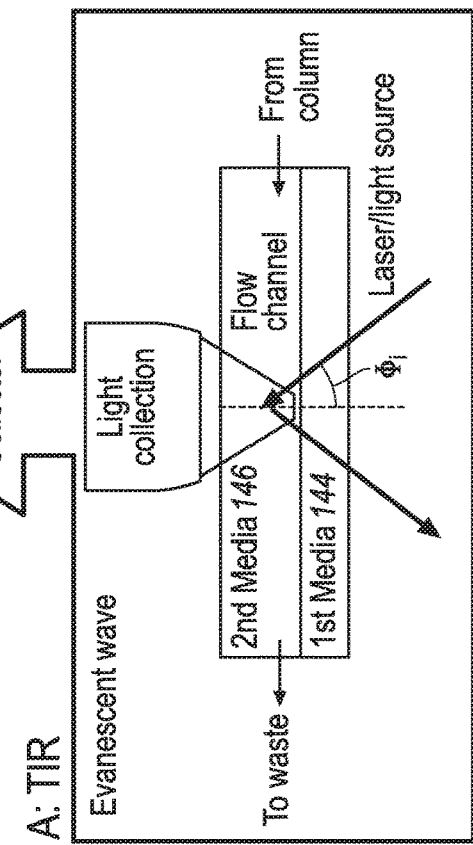
FIG. 11

SYSTEM FOR DETECTING LIQUID ANALYTES

CROSS-REFERENCE TO RELATED APPLICATIONS

This application claims priority to Provisional Application No. 62/514,375, filed on Jun. 2, 2017, which application is hereby incorporated herein by reference in its entirety.

FIELD

The present disclosure relates to a system and method for rapidly detecting, identifying, and quantifying target constituent liquid analytes in blood, urine, water, saliva and other liquid phase samples. A device for use in the system combines a liquid chromatography cartridge with an enhanced optical interface for liquid spectroscopy analysis of the separated analyte constituents. The device can be used to interrogate liquid samples such as urine, serum or secretions, and liquid environmental samples. A liquid chromatography cartridge can also be referred to herein as a sample cartridge.

BACKGROUND

This section provides background information related to the present disclosure which is not necessarily prior art.

Liquid chromatography (LC) is a technique used to separate a sample into its individual parts. Liquid chromatography systems are large laboratory instruments with trained technicians and large, expensive separator columns. Components of a mixture are separated in a separator column based on each component's affinity for a mobile phase and a stationary phase. The mobile phase is a liquid with which the sample is mixed, used to transport the sample through the stationary phase. The stationary phase is an adsorbent solid material, such as beads, a matrix or other physical structure, arranged in the separator column, through which the mobile phase is passed. Chromatography based upon molecular polarity is effective because different components within a mixture are attracted to the adsorbent surface of the stationary phase with varying degrees depending on each components polarity and its unique structural characteristics, and its interaction with the mobile phase. The separation that is achieved using column chromatography is based on factors that are associated with the sample. A component that is more attracted to the stationary phase will migrate down the separator column at a slower rate than a component that has a higher affinity for the mobile phase. Also, the efficacy of the separation is dependent on the nature of the adsorbent solid used and the polarity of the mobile phase solvent. If the components are of different polarities and a mobile phase of a distinct polarity is passed through the separator column, one component will migrate through the separator column faster than the other. The separator columns are typically packed with beads with absorbent chemistry to induce separation. Because molecules of the same compound will move in groups, the compounds are separated into distinct bands within the separator column. This provides the ability of liquid chromatography (LC) to both separate and concentrate like compounds. If the components being separated are colored, their corresponding bands can be seen. Otherwise, as in high-performance liquid chromatography (HPLC), the presence of the bands is detected using other instrumental analysis techniques such as UV-VIS spectroscopy. UV-VIS spectroscopy provides a means of detecting separation of constituents but does not identify the components. To determine the composition of each separated constituent, either colored separate components or reference analytes are required.

DRAWINGS

The drawings described herein are for illustrative purposes only of selected examples and not all possible implementations and are not intended to limit the scope of the present disclosure.

FIG. 11 illustrates an example liquid chromatography unit and two alternative configurations for the collector.

SUMMARY

Figure 1:
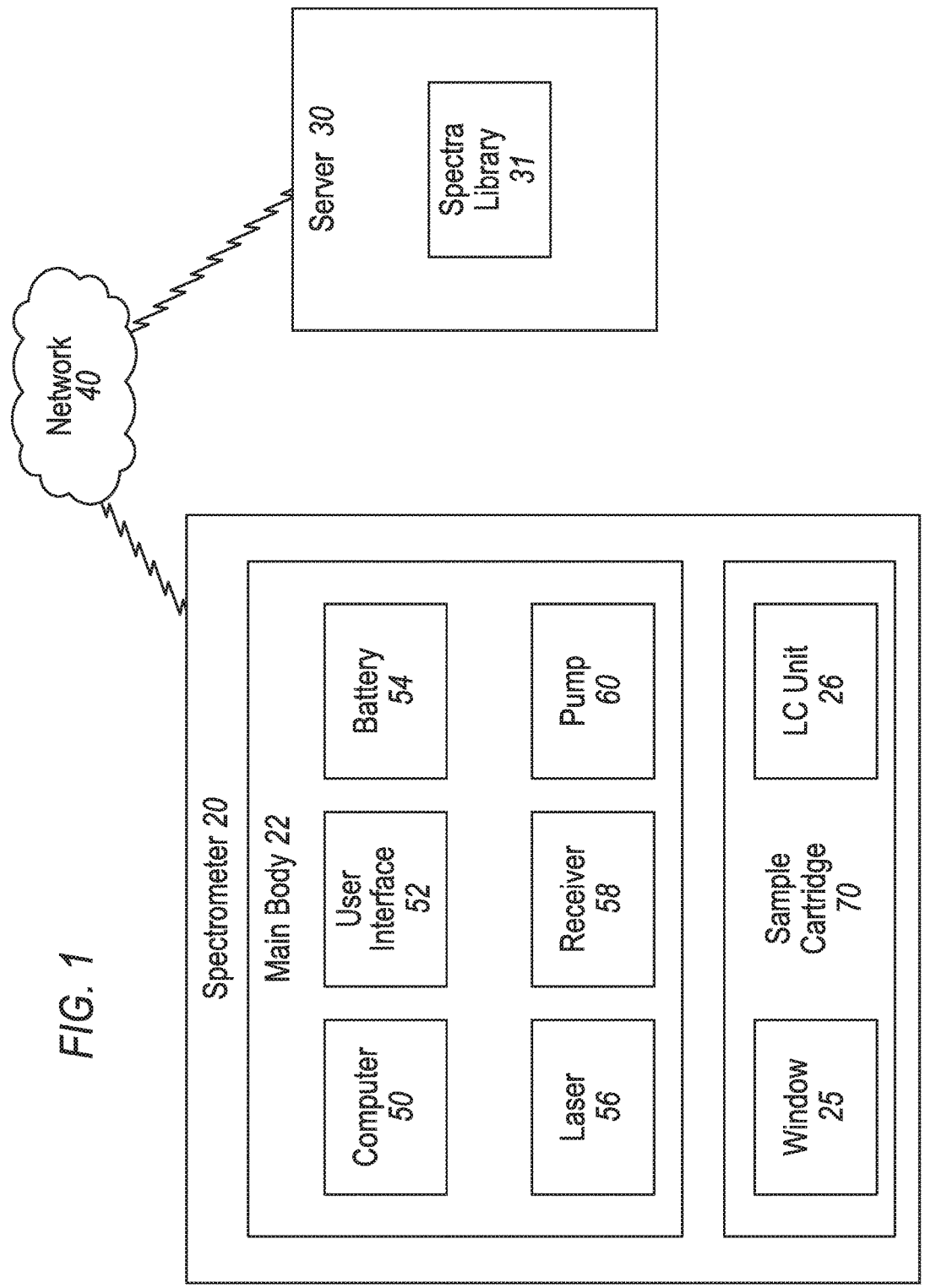
FIG. 1 illustrates an example spectrometer system for performing liquid chromatography on a sample.

This section provides a general summary of the disclosure, and is not a comprehensive disclosure of its full scope or all its features.

A liquid chromatographic (LC) spectroscopy device, which may be portable, is arranged to interface with a disposable liquid chromatography cartridge (sample cartridge) and enables the detection of normally undetectable low concentration constituents in analytes in blood, urine, sputum, and other liquid phase samples. The sample cartridge concentrates ultralow concentrations of compounds which are analyzed downstream by an integrated optical train to the sample cartridge. A spectroscopy system, which may be a Raman Spectroscopy system interrogates separated and concentrated compounds in the sample cartridge. The spectroscopy system directly analyzes the molecular fingerprint of the concentrated and separated compounds. Further, the sample cartridge provides enhanced separation via microfluidic geometries. An internal reflection spectroscopy optical system may be integrated into the sample cartridge enhances the spectroscopy signal providing greater sensitivity. This allows more direct measurement and quantification at a point of optical interrogation. The point of optical interrogation is a location within the sample cartridge where the separated analytes can be subjected to spectroscopic analysis.

The liquid chromatographic (LC) spectroscopy device incorporates signal processing and identification algorithms for signal conditioning and target detection. The liquid spectroscopy device may further transmit an initial analysis via wired or wireless communications such as Bluetooth®/Wi-Fi® or Internet onboard communication to a server wherein the initial analysis is further scrutinized and the identification algorithms for signal conditioning and target detection are applied. A liquid chromatographic (LC) spectroscopy device can also be referred to herein as a spectrometer or a LC spectrometer.

Further areas of applicability will become apparent from the description provided herein. The description and specific examples in this summary are intended for purposes of illustration only and are not intended to limit the scope of the present disclosure.

DETAILED DESCRIPTION

Examples of a LC spectrometer will now be described more fully with reference to the accompanying drawings. It will be apparent to those skilled in the art that specific details need not be employed, that examples may be embodied in many different forms and that neither should be construed to limit the scope of the disclosure. In some examples, well-known processes, well-known structures, and well-known technologies are not described in detail.

The terminology used herein is for describing examples only and is not intended to be limiting. As used herein, the singular forms "a," "an," and "the" may include the plural forms as well, unless the context clearly indicates otherwise. The terms "comprises," "comprising," "including," and "having," are inclusive and therefore specify the presence of recited structure(s) or step(s); for example, the stated features, integers, steps, operations, groups elements, and/or components, but do not preclude the presence or addition of additional structure(s) or step(s) thereof. The methods, steps, processes, and operations described herein are not to be construed as necessarily requiring performance in the stated or any particular order discussed or illustrated, unless specifically identified as an order of performance. It is also to be understood that additional, alternative or equivalent steps may be employed.

When structure is referred to as being "on," "engaged to," "connected to," or "coupled to" other structure, it may be directly or indirectly (i.e., via intervening structure) on, engaged, connected or coupled to the other structure. In contrast, when structure is referred to as being "directly on," "directly engaged to," "directly connected to," or "directly coupled to" the other structure, there may be no intervening structure present. Other words used to describe the relationship between elements should be interpreted in a like fashion (e.g., "between" versus "directly between," "adjacent" versus "directly adjacent"). As used herein, the term "and/or" includes any and all combinations of one or more of the associated referenced items.

Terms of degree (e.g., first, second, third) which are used herein to describe various structure or steps are not intended to be limiting. These terms are used to distinguish one structure or step from other structure or steps, and do not imply a sequence or order unless clearly indicated by the context of their usage. Thus, a first structure or step similarly may be termed a second structure or step without departing from the teachings of the example examples. Likewise, spatially relative terms (e.g., "inner," "outer," "beneath," "below," "lower," "above," "upper") which are used herein to describe the relative special relationship of one structure or step to other structure or step(s) may encompass orientations of the device or its operation that are different than depicted in the figures. For example, if a figure is turned over, structure described as "below" or "beneath" other structure would then be oriented "above" the other structure without materially affecting its special relationship or operation. The structure may be otherwise oriented (e.g. rotated 90° or at other orientations) and the spatially relative descriptors used herein interpreted accordingly.

In the context of the present disclosure Raman spectroscopy is described as a reagentless, non-destructive, technique that can provide a unique spectral fingerprint of a chemical and/or molecule allowing for target identification. With this technique, a sample is irradiated with a specific wavelength of light whereby a small component, for example, 1 in $10^7$ photons, is in-elastically scattered (at wavelengths shifted from the incident radiation). The inelastic scattering of photons, due to molecular vibrations that change the molecule's polarizability, provide chemical and structural information uniquely characteristic of the targeted substance. Raman Spectroscopy can be useful in fully characterizing a material's composition, and allows for relatively fast identification of unknown materials with the use of a Raman spectral database.

Raman Spectroscopy has a high potential for direct analysis of analytes for specific targets such as drugs, blood serum chemical components, contaminants and other liquid born compounds. The term "analyte" for purposes of this disclosure, means is a substance whose chemical constituents are being identified and measured. As a non-limiting example of this spectroscopy system, a portable or point of care Raman-based liquid chromatography spectroscopy device combined with a sample cartridge could be used to reliably and rapidly assess vitamin metabolites such as, for example, Vitamin D.

Vitamin D deficiency is an emerging public health problem. Vitamin D in the body is derived from dietary sources (D2 from plants and D3 from animals) and is synthesized in the skin (D3 from light absorbed by a precursor molecule 7-dehydrocholesterol). The conversion of vitamin D into a "biologically active form" requires 25-hydroxylation in the liver to form 25-hydroxyvitamin D and 1α-hydroxylation primarily in the kidney to form 1,25-dihydroyvitamin D (studies have suggested that 25(OH)D is hydroxylated to 1,25(OH)$_2$D in tissue such as breast, colon, and prostate).

The biologically active metabolite, 1,25-dihydroxy vitamin D, binds to nuclear vitamin receptors in bone, intestine, as well as other tissue. Decreased levels of this metabolite are observed in conditions such as hypoparathyroidism and chronic renal failure, while elevated levels are present in conditions such sarcoidosis and hyperparathyroidism.

Due to the short half-life of 1,25-dihydroxy vitamin D (~15 hours) and regulation through concentrations of serum calcium, phosphorus, and parathyroid hormone, 25-hydroxyvitamin D is used for detecting vitamin D deficiency. Serum levels of 25-hydroxyvitamin D, with circulating half-life of 15 days, better reflect overall vitamin D status via dietary intake and solar exposure. While 1,25-dihydroxy vitamin D levels may better reflect the biologically significant metabolite that can be used to determine specific disease status.

Isomerization of 25-hydroxyvitamin D (25-OH D) produces biologically inactive 3-epi analogs of 25-OH D2 and 25-OH D3. 25-hydroxy vitamin D3 epimer (C3 epimer), originally found in infants, has been detected in adults as well. For more accurate vitamin D status, it is desired to distinguish between these forms. The inclusion of 3-epi analogs in measurements could contribute to falsely high levels of vitamin D.

Drug tests designed to detect and deter abuse of illicit and performance-enhancing drugs by employees and by athletes is another area where a portable, Raman spectrometer can be used to advantage. As one example, a portable Raman spectrometer can be an effective tool for identifying the presence of opiates in human urine samples.

Drug testing begins with taking a urine or blood sample. Since many drugs are only detectable for a few hours to a few days, detection is often difficult. In addition, as part of sports doping policy, specimens are not refrigerated or frozen until they reach the laboratory. With worldwide testing, samples are sent all over the world and there can be delays in delivering them to labs of several days. This can result in sample degradation or bacterial contamination which can influence test results. A portable, rapid point-of-need screening method allows cost-effective, no-notice testing of athletes and workplace employees as a first measure of evaluation.

Liquid Chromatographic Raman Spectroscopy has significant benefits over existing technologies such as Immunoassays, GC-MS (gas chromatography-mass spectrometry) and LC-MS (liquid chromatography-mass spectrometry) in that (1) it can be readily adapted to a mobile platform, (2) it may offer specificity greater than that of gold standard methods, (3) it can provide rapid automated detection and identification of unknown compounds and (4) it can provide both molecular signatures as well as structural signature that may provide direct evidence of blood transfusion due to membrane changes.

FIG. 1 illustrates a system 10 for Raman-based liquid chromatography. The system 10 includes a spectrometer 20 communicatively coupled with a server 30 via a network 40.

The spectrometer 20 includes a main body 22 including a computer 50, a user interface 52 and a battery 54, a laser 56, and a receiver 58. The main body may further include a pump 60. The spectrometer 20 further includes a sample cartridge 70. The main body 22 is configured to receive the sample cartridge 70 including a sample to be analyzed. When the cartridge 70 is inserted into the main body 22, the pump 60 in the main body 22 may be in fluid communication with a liquid chromatography (LC) unit 26 in the cartridge 70. The pump 60 may generate pressure to transport a sample through the liquid chromatography (LC) unit 26 to separate a sample into constituent parts.

Alternatively, the sample cartridge 70 may include one or more blisters containing a liquid solvent. A mechanical piston included in the sample cartridge 70 may be actuated to integrate the solvent with the liquid sample.

As another alternative, the sample cartridge 70 may include a micropump fluidly coupled to an internal reservoir and/or an external sampling port which can transport a liquid solvent and/or analyte through the liquid chromatography (LC) unit 26.

After separation, the spectrometer 20 illuminates the constituent parts of the sample with use of the laser 56, and via a port 25 formed in the sample cartridge 70. The spectrometer 20 collects Raman back-scattered light via the receiver 58. The computer 50 can then analyze the back-scattered light to determine the presence of analytes and/or transmit the data to the server 30 for analysis.

The sample cartridge 70 includes a case 24, a liquid chromatography (LC) unit 26 and the port 25. The port 25 may be a hole formed by the case 24. As described in detail below, the LC unit 26 is arranged and includes components for separating a sample into constituent parts. The port 25 permits irradiation by the laser of the sample by the laser 56 in the main body 22 and collection of back-scattered light by the receiver 58.

The computer 50 includes a processor and memory including instructions for programming the computer 50. The computer 50 is communicatively coupled with the user interface 52, the laser 56, the receiver 58 and the pump 60. The computer 50 is programmed to control the pump 60 and the laser 56 to gather Raman data from the sample in the sample cartridge 70. The computer 50 is further programmed to receive data from the receiver 58, analyze the data and/or transmit the data to the server 30 for analysis. Analyzing the data includes identifying spectra included in the data and comparing the spectra to representative spectra that may be maintained in a spectra library 31 on the server 30 or on the computer 50 included in the spectrometer 20. The battery 54 provides electrical energy to the spectrometer 20 and may be a standard battery such as a lead-acid, nickel-cadmium, lithium-ion battery etc.

The computer 50 may further be programmed to receive and execute instructions from the user interface 52. For example, the computer 50 may receive instructions from the user interface 52 to initiate an analysis of a sample. Based on the received instructions, the computer 50 may generate and send instructions to the pump 60, laser 56 and receiver 58 to measure a sample, and collect data from the measurement.

The server 30 includes a processor and a memory including instructions for programming the server 30. The server 30 may further include and be programmed to maintain a spectra library 31. The spectra library 31 may include sample Raman data spectra of analytes that may be targeted for identification by the spectrometer 20. As described in additional detail below, the server 30 is programmed to receive data from the spectrometer 20 and identify, based on the data from the sample submitted to the sample cartridge 70, constituents of the sample. The server 30 may, for example, compare the received data with example spectra in the spectra library 31. The server 30 may determine the identity of constituents in the sample based on comparisons between the data and the example spectra.

The network 40 is one or more mechanisms by which the spectrometer 20 and the server 30 communicate with each other, and may be one or more of various wired or wireless communication mechanisms, including any desired combination of wired (e.g., cable and fiber) and/or wireless (e.g., cellular, wireless, satellite, microwave and radio frequency) communication mechanisms and any desired network topology (or topologies when multiple communication mechanisms are utilized). Exemplary communication networks include wireless communication networks (e.g., using one or more of cellular, Bluetooth®, IEEE 802.11, etc.), local area networks (LAN) and/or wide area networks (WAN), including the Internet, providing data communication services.

The types of wireless communications may include one or more of cellular, Bluetooth®, IEEE 802.11 (typically, Wi-Fi®), dedicated short range communications (DSRC), two-way satellite (e.g., emergency services), one-way satellite (e.g., receiving digital audio radio broadcasts), AM/FM radio, etc.

Figure 2:
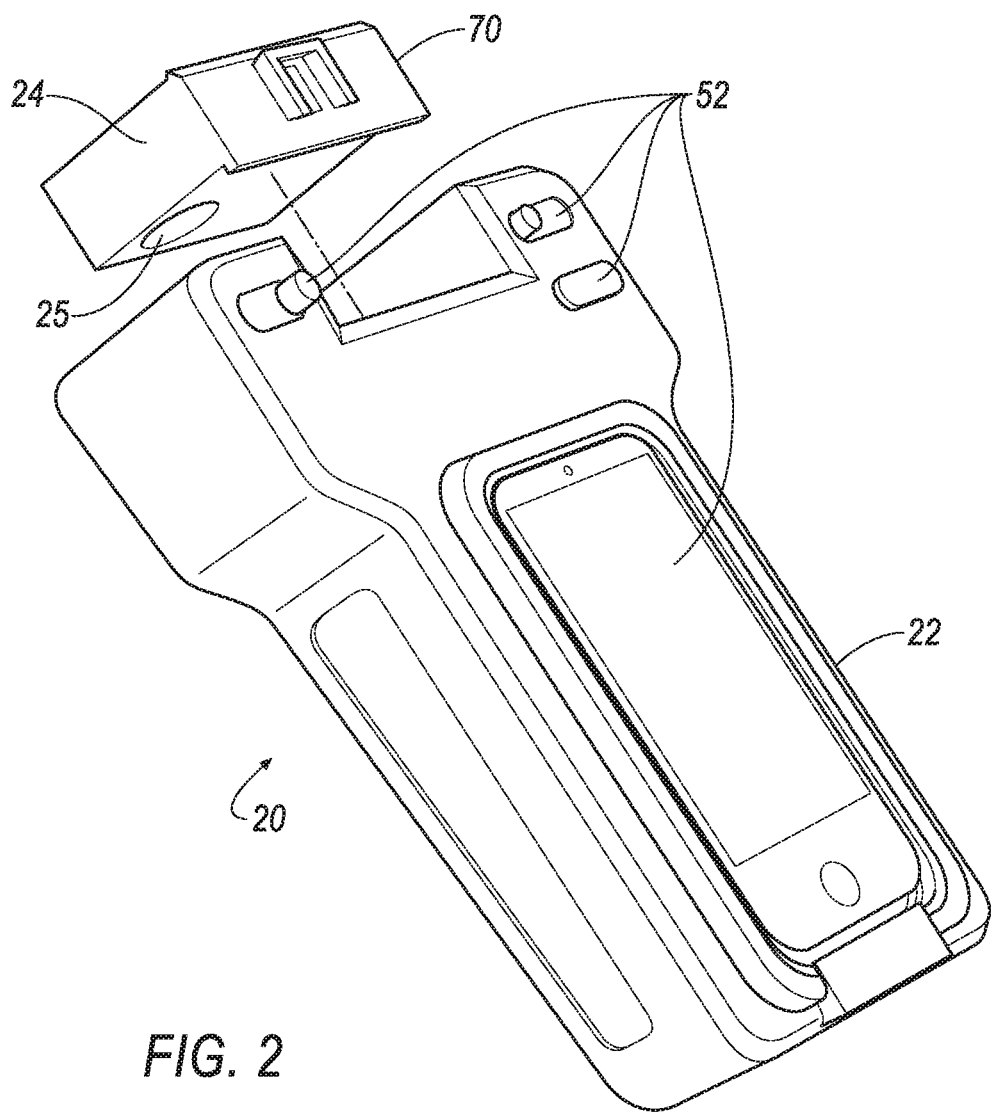
FIG. 2 illustrates an example handheld liquid chromatography device including a main body and a sample cartridge.

FIG. 2 illustrates an example hand-held spectrometer 20. The spectrometer 20 comprises a reusable main body 22 and the sample cartridge 70.

The main body 22 contains the components necessary for spectral acquisition such as Raman spectral acquisition. As described with regard to FIG. 1, the components include the computer 50, the user interface 52, the laser 56, the receiver 58 and the pump 60.

The main body 22 is arranged to receive the sample cartridge 70 and perform Raman spectral acquisition on a sample processed by the sample cartridge 70. The sample cartridge 70 receives a sample and may further receive a mobile phase. The sample may be a liquid such as blood or urine that may include several components including a target analyte. The target analyte is a chemical compound that a user is seeking to identify in the sample.

The sample cartridge 70 performs a separation process to separate the sample into constituent components. As described below, the separation process may be adapted based on the type of sample to be analyzed. The sample cartridge 70 includes a liquid chromatography (LC) unit 26 to perform the separation.

The sample cartridge 70 is enclosed in a case 24. The case 24 forms the port 25. The port 25 is a hole through the case 24 that permits the laser 56 in the main body 22 to irradiate the sample and the receiver 58 to collect of back-scattered light from the sample. In some cases, the port 25 may be closed with glass, a clear polymer or other material that allows light to pass.

The sample cartridge 70 may be disposable. That is, a sample cartridge 70 may be used to analyze a single sample, and then disposed to avoid contamination between samples. Further, a sample cartridge 70 may be specific for a type of analysis. For example, a sample cartridge 70 for detecting vitamin D in blood may be different from a sample cartridge 70 for detecting an opiate in urine.

Figure 3:
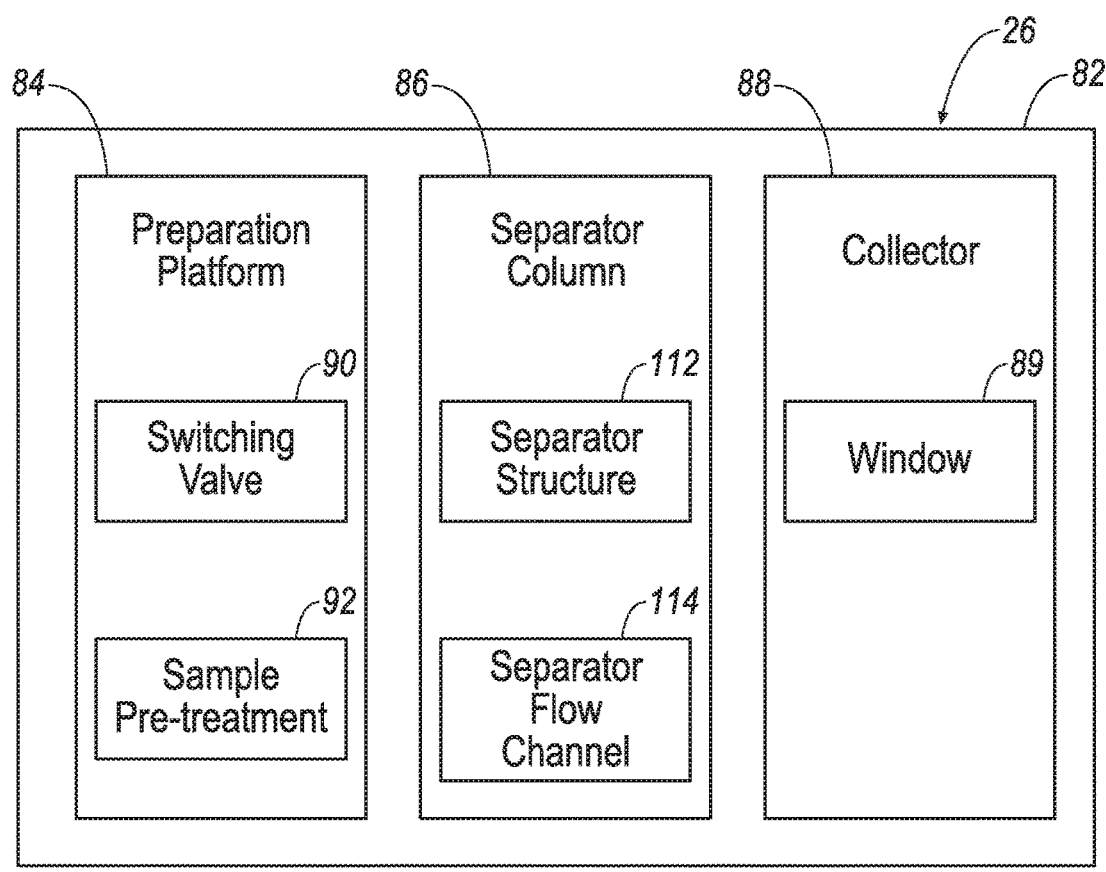
FIG. 3 is a schematic diagram of liquid chromatography (LC) unit included in the sample cartridge of FIGS. 1 and 2.

FIG. 3 is a schematic diagram of an example LC unit 26. The LC unit 26 includes a microfluidic chip 82. The microfluidic chip 82 can be referred to herein as the chip 82. The LC unit 26 further includes a preparation platform 84, a separator column 86 and a collector 88. Some or all the preparation platform 84, the separator column 86 and the collector 88 may be formed in the chip 82 or supported on the chip 82. In some cases, one or more of the preparation platform 84, the separator column 86 and the collector 88, or a portion of one of these components, may be formed separately from the chip 82.

In one example, the LC unit 26 may be a microfluidic system for receiving and processing a liquid sample. The LC unit 26 may be built on the chip 82. The chip 82 is typically a polymer but may also be constructed of other materials such as silicon or a ceramic. In practice, the design of the LC unit 26 may be specific for a type of liquid sample that is targeted. For example, a LC unit 26 for detecting vitamin D in blood may be different from a LC unit 26 for detecting an opiate in urine. Different examples are presented below in reference to FIG. 4.

The chip 82 is used to support and/or form the preparation platform 84, the separator column 86 and the collector 88. The preparation platform 84 is used to prepare a sample for submission to the separator column 86 and may include a switch valve 90 (see FIG. 4) and/or one or more sample pre-treatment chambers 92. The switch valve 90 can also be referred to herein as the valve 90. The preparation platform 84 may remove one or more substances from the sample that may interfere with the operation of the separator column 86. Further, the preparation platform 84 may be used to prepare a measured amount of the sample to the separator column 86.

The separator column 86 is a passage through which a liquid sample is passed to separate the constituent components of the sample. As described in additional detail below, the separator column 86 includes a separator structure 112 and a separator flow channel 114. The separator structure 112 may comprise particles or beads packed together in a column, or may comprise a monolithic structure formed on a substrate. The separator structure 112 may be treated with, or may otherwise support the stationary phase. The separator flow channel 114 is a channel through the stationary phase through which the sample flows.

The collector 88 is a chamber through which the separated sample (i.e., the sample as it exits the separator column 86) flows. The collector 88 includes an area including a second optically transparent window 89 for analyte detection. The second optically transparent window 89 is a structure that allows the passage of optical beams (e.g. laser beams) to irradiate the separated sample and further allows back-scattered light to irradiate out of the collector 88. The receiver 58 in the main body 22 of the spectrometer 20 may be arranged to capture the back-scattered light as it exits the collector 88 through the second optically transparent window 89.

Figure 4A:
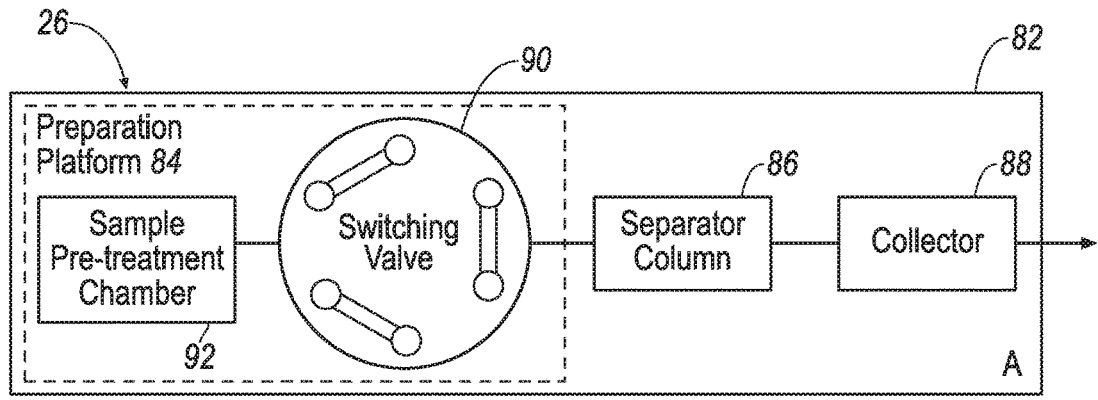
FIG. 4A is schematic diagram of an example liquid chromatography unit.
Figure 4B:
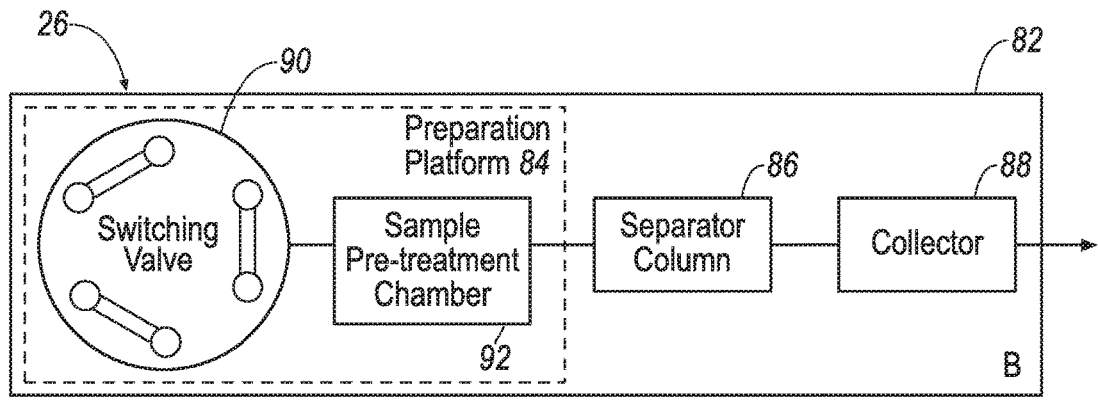
FIG. 4B is a schematic diagram of an example liquid chromatography unit.
Figure 4C:
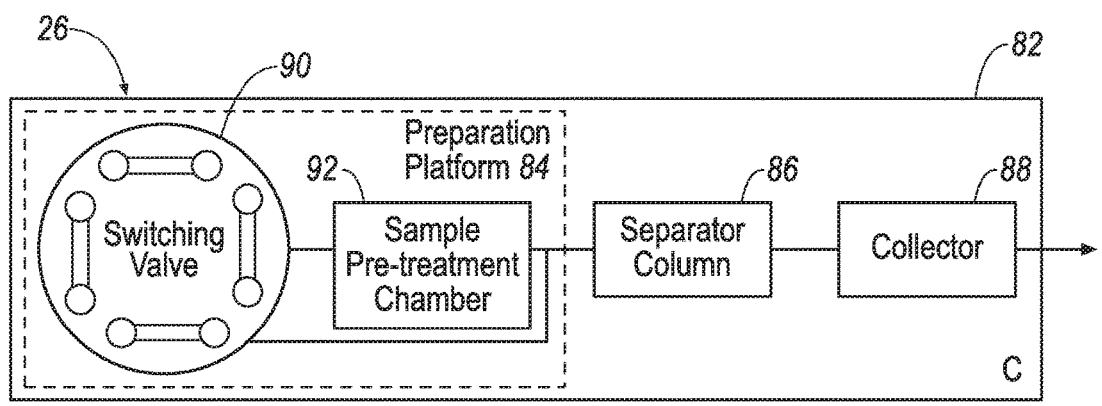
FIG. 4C is a schematic diagram of an example liquid chromatography unit.

FIGS. 4A-4C illustrate three different example configurations for the LC unit 26. Depending on the nature of sample pre-treatment requirements, the LC unit 26 can be configured to accommodate these requirements. For example, multiple pre-treatment zones in the LC unit 26 may be necessary to (1) extract contaminants or unwanted substances from the sample or (2) to extract the analyte or analytes of interest from the sample to concentrate in a homogenous or more homogenous solution to inject into the separator column 86. FIGS. 4D-4G illustrate alternative configurations and switching positions of the valve 90.

Figure 4D:
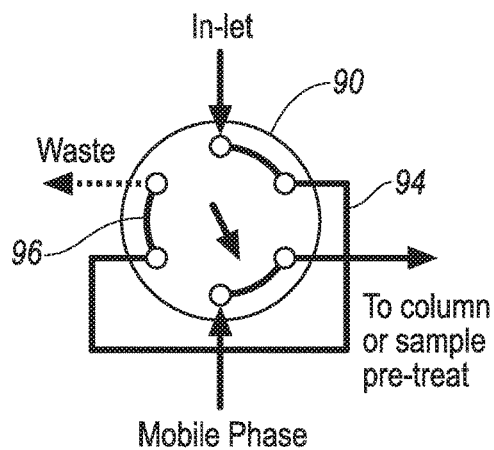
FIG. 4D is a diagram of an example switching valve configuration.
Figure 4E:
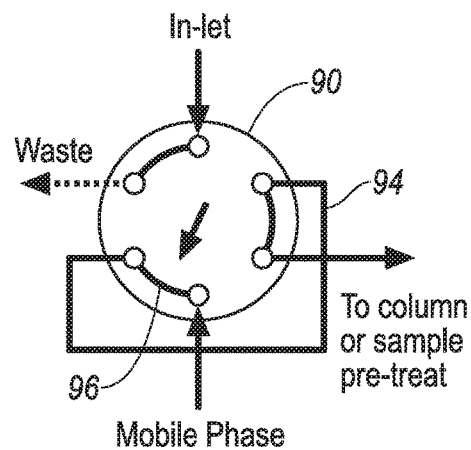
FIG. 4E is a diagram of an example switching valve configuration.

FIG. 4A illustrates the sample LC unit 26 configured with a 6 port switch valve 90. In this configuration, a previously pre-treated sample can be injected onto the separator column 86. With the valve 90 in the position as shown in FIG. 4D, the pre-treated sample flows through an external loop 94 while a carrier solvent (the mobile phase) flows directly to the separator column 86. When the valve 90 is switched to the position as shown in FIG. 4E, the sample contained in the external loop 94 and valve flow passage 96 is injected into the separator column 86. In this manner, a fixed volume of the sample, i.e., the volume of the sample contained in the external loop 94 and valve flow passage 96, is injected into the separator column 86. As an example, the fixed volume may be in a range from microliters to milliliters. The valve 90 may be actuated electromechanically, such as by magnetic actuation, piezo-electric actuation, a micropump, etc. Alternatively, individual blisters may be actuated, for example, with mechanical pistons.

FIG. 4B illustrates a configuration of the sample LC unit 26 including the 6 port switch valve 90. In this configuration, the sample can be injected into the sample pre-treatment 92. The sample then flows, together with the mobile phase directly to the separator column 86.

Figure 4F:
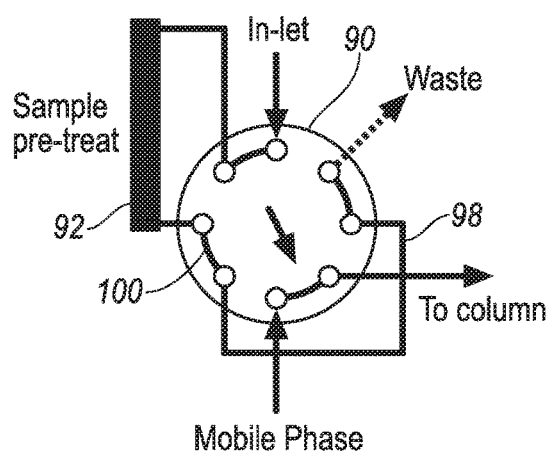
FIG. 4F is a diagram of an example switching valve configuration.
Figure 4G:
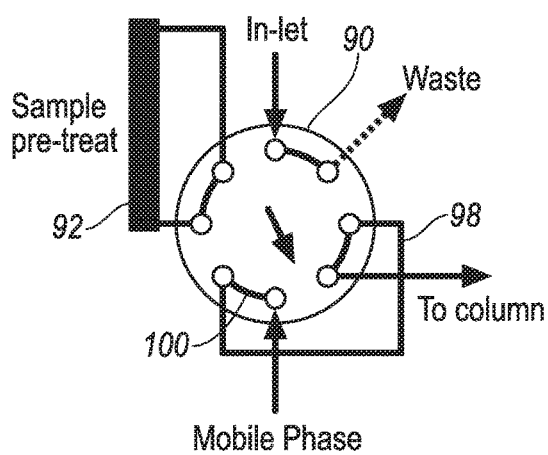
FIG. 4G is a diagram of an example switching valve configuration.

FIG. 4C illustrates a configuration of the sample LC unit 26 including an 8 port switch valve 90. With the 8 port switch valve 90 in a position as shown in FIG. 4F, the sample flows through an external loop 98 that contains the sample pre-treatment chamber 92, while the mobile phase flows directly to the separator column 86. When the valve 90 is switched to the position of FIG. 4G, the sample contained in the external loop 98 and valve flow passage 100 is injected into the separator column 86. This configuration allows the sample pre-treatment chamber 92 to be exposed to a different solvent than that of the mobile phase. The switching valve 90 may also be replaced by a series of flow channels to incorporate a linear actuated (as opposed to a rotatory) method of directing/redirecting fluid flow through the sample LC unit 26.

Figure 5:
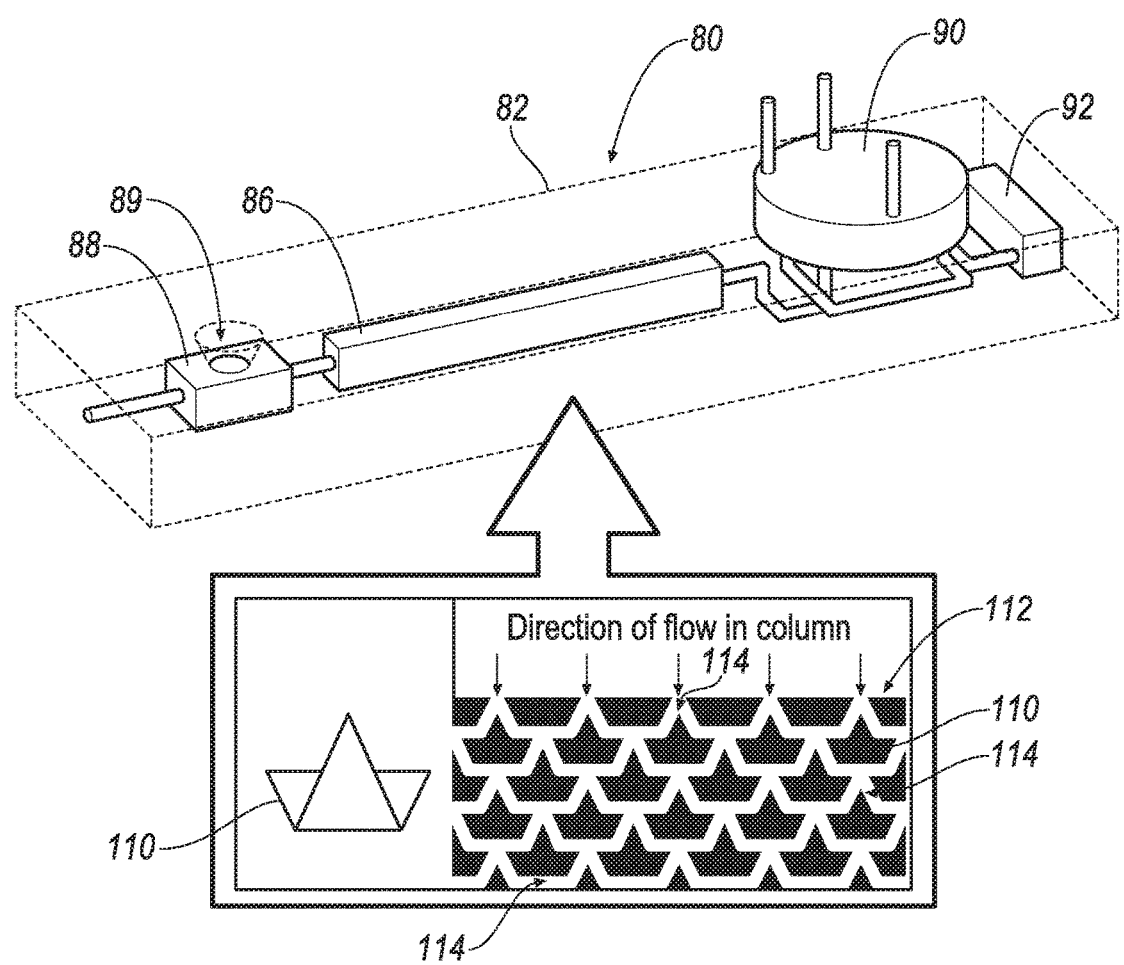
FIG. 5 illustrates an example liquid chromatography unit including an example separator structure in the separator column.

FIG. 5 illustrates an example chip 82. The example chip 82 forms or supports one or more of a switch valve 90, one or more sample pre-treatment chambers 92, the separator column 86 and the collector 88. The separator column 86 comprises a separator structure 112 comprising a plurality of three-triangular pillars 110.

Conventional liquid chromatography (LC) columns are typically packed with particles. Porous packings have been favored. However, mass transfer of solutes is hindered by pore diffusion. Reducing particle size can reduce diffusion path length. However, smaller particles means increased pressure drop across the column. Large pores can enhance mass transfer but reduce surface area.

To achieve high resolution separation, a scalable three-triangular pillar 110 is utilized in the separator column 86. FIG. 5 shows the geometry of the three-triangular pillar 110 composed of three triangles. A plurality of three-triangular pillars 110 are combined to form the separator structure 112. Spaces between the three-triangular pillars 110 form a separator flow channel 114 through which the sample flows. The separator flow channel 114 results in fluidic interaction with all sides of the three-triangular pillars 110 providing a more efficient high surface area structure with reduced shear forces and ebbying effects. The three-triangular pillars 110 may be scaled in size to adjust flow and surface area.

In the separator column 86, the separator structure 112 will be bonded with a stationary phase. The stationary phase includes a reversed phase stationary phase (non-endcapped or endcapped), wherein the reversed phase stationary phase may be polymer-based or silica-based. Any reversed phase stationary phase known in the art may be used, such as Pentafluorophenyl (F5), C-1, C-4, C-8, and C-18. The sample's differential affinity for the solvent and the stationary phase enables separation to occur. As an example, a reverse phase C-18 column utilizes octadecylsilane bonded to a support material. The chain length of the functional group influences the hydrophobicity of the sorbent phase and thus the retention time of the analyte. With reverse phase chromatography the stationary phase is non-polar while the mobile phase is polar. Compounds in the sample that are similar in polarity to the stationary phase will be delayed because they are more strongly attracted to the particles. Compounds whose polarity is similar to that of the mobile phase will be preferentially attracted to it and move faster. The three-triangular support packing may be used in an integrated sample pre-treatment chamber 92 and functionalized with the warranted chemistry.

Figure 6:
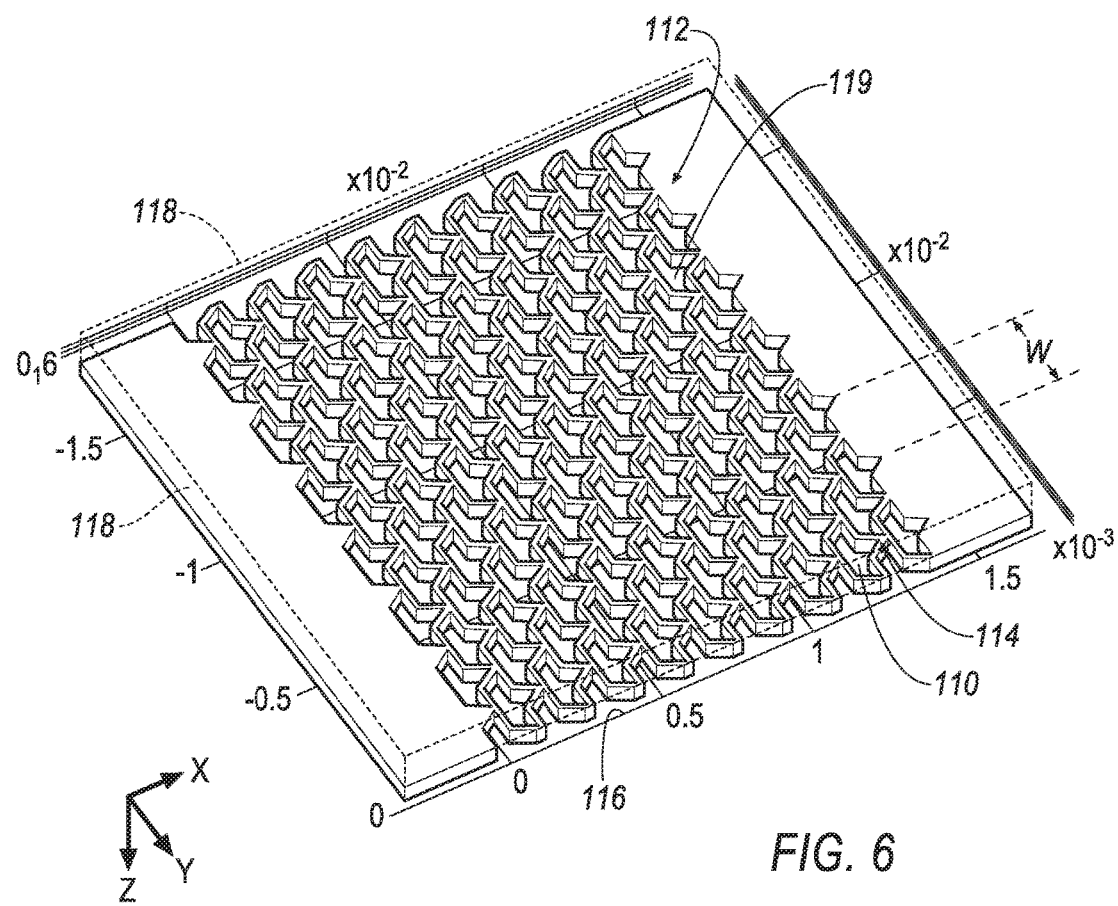
FIG. 6 illustrates an example separator structure.

FIG. 6, illustrates the separator structure 112 creating a flow that interacts with all sides of the three-triangular pillars 110 that optimizes separation with selective absorbent chemistry that inhibits unwanted constituents. The three-triangular pillars 110 may be formed on a substrate 116. The substrate 116 may be a polymer and the three-triangular pillars 110 may be formed in the substrate, for example, by an embossing process. The three-triangular pillars 110 are arranged in rows. A spacing from a center of one three-triangular pillar 110 to an adjacent three-triangular pillar 110 is a distance w. The rows are stacked, with each subsequent row shifted by a distance w/2 from the previous row. A subsequent row is a row directly next to and under or above a previous row. A top plate 118 or other closing mechanism is arranged on a top side 119 of the separator structure 112 to form a top of the separator flow channel 114.

Figure 7A:
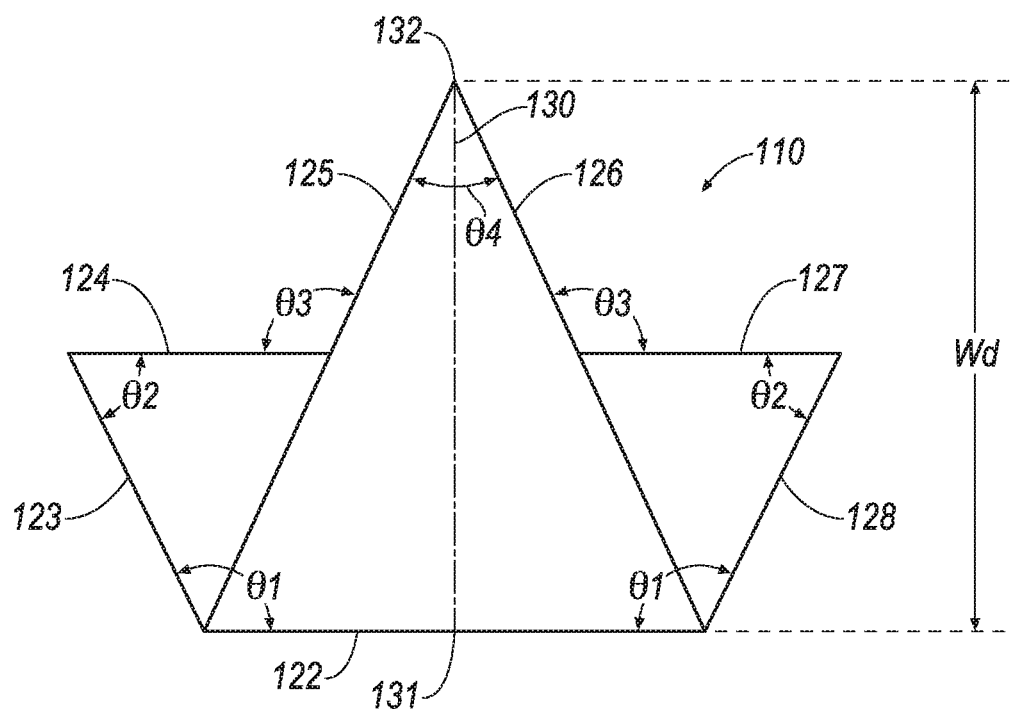
FIG. 7 is a top view of an example three-triangular pillar.
FIG. 7B is a perspective view of the example three-triangular pillar of FIG. 7A.
FIG. 7C is a top view of a section of an example separator structure.

FIG. 7A is a top view of a three-triangular pillar 110. As seen from the top, the three-triangular pillar 110 comprises a seven-sided structure including first-seventh sides 122, 123, 124, 125, 126, 127, 128. The three-triangular pillar 110 is symmetrical around a centerline 130. The centerline 130 extends perpendicularly away from a middle 131 of the first side 122. The first side 122 is connected to the second side 123 at a first end and a seventh side 128 at a second end. The second side 123 and seventh side 128 extend away from the first side 122 in opposite directions, each forming an obtuse angle θ1 with the first side 122.

The second side 123 extends between the first side 122 and the third side 124. The third side 124 extends in a direction parallel to the first side 122 and towards the centerline 130, forming an acute angle θ2 with the second side 123. The angle θ2 equals 180° minus θ1. Similarly, the seventh side 128 extends between the first side 122 and connects to the sixth side 127. The sixth side 127 extends in a direction parallel to the first side 122 towards the centerline 130.

The third side 124 extends between the second side 123 to a fourth side 125. The fourth side 125 extends in a direction away from the first side 122 and toward the centerline 130, forming an angle θ3 with the third side 124. The direction of the third side 124 is parallel to the direction of the seventh side 128.

Similarly, the sixth side 126 extends from the seventh side 128 to a fifth side 126. The fifth side 126 extends in a direction away from the first side 122 and toward the centerline 130. The direction of the fifth side is parallel to the direction of the second side 123. The fifth and fourth sides 126, 125 connect at an apex 132 of the three-triangular pillar 110, forming an angle θ4. A width "wd" of the three-triangular pillar 110 is a distance from the first side 122 to the apex 132 along the centerline 130. The width "wd" is in a range from five micrometers to 100 millimeters or greater.

In an example three-triangular pillar 110:
 the angle θ1 may be in a range from 95° to 155°, and is typically 124°,
 the angle θ2 is 180° minus θ1, and is typically 56°,
 the angle θ3 is substantially equal to the angle θ1, and
 the angle θ4 is determined based on the angles θ1, θ2 and θ3.

Figure 7B:
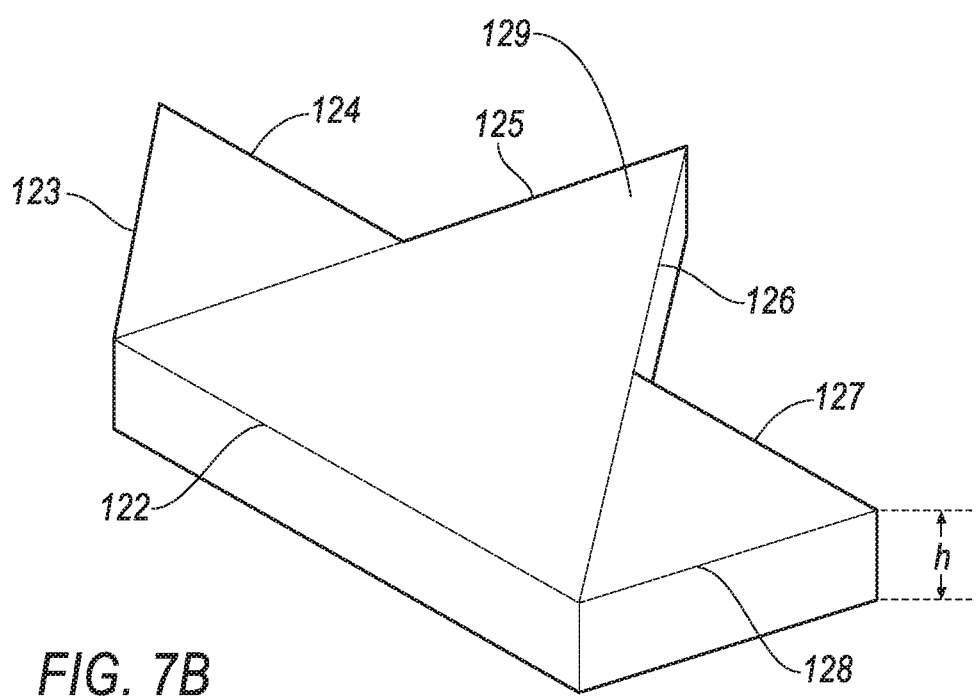

FIG. 7B is a perspective view of the three-triangular pillar 110 of FIG. 7A. A height "h" of the three-triangular pillar 110 may be in a range from 100 micrometers to several millimeters, with a typical height "h" of 500 micrometers. A top side 129 of each of the three-triangular pillars 110 forms in part the top side 119 of the separator structure 112 (FIG. 6).

Figure 7C:
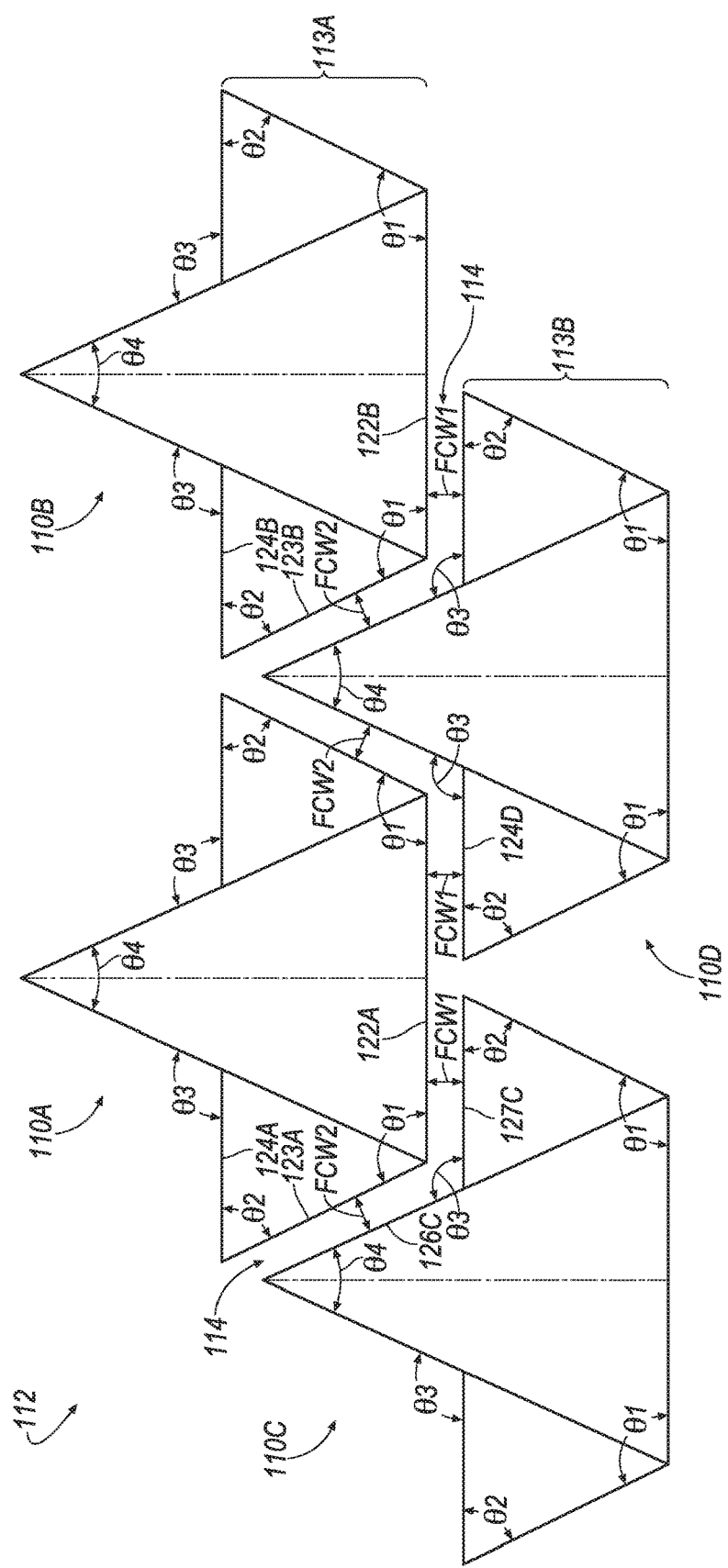

FIG. 7C is a top view of a section of the exemplary separator structure 112 including first, second, third and fourth three-triangular pillars 110A, 110B, 110C, 110D organized in two rows. A first row 113A includes the first and second three-triangular pillars 110A, 110B. A second row 113B includes third and fourth three-triangular pillars 110C, 110D. The second row 113B is arranged below the first row 113A such that the separator flow channel 114 has a flow channel width of fcw1 between, e.g., first side 122A of the first three-triangular pillar 110A and the sixth side 127C of the third three-triangular pillar 110C. The first flow channel width fcw1 may be in a range of one micrometers to 100 micrometers, with a typical width of 10 micrometers.

Further, the first row 113A and second row 113B are arranged laterally, one to the other, such that the separator flow channel 114 has a second flow channel width fcw2 between, for example, the fifth side 126C of the third three-triangular pillar 110C and the second side 123A of the first three-triangular pillar 110A. The second flow channel width fcw2 may be in a range one micrometer to 100 micrometers, with a typical width of 10 micrometers. In some cases, the first and second rows 113A, 113B may be arranged, such that fcw1 is substantially equal to fcw2.

The separator structure 112 and the three-triangular pillars 110 included in the separator structure 112 are scalable. Dimensions can be adjusted to accommodate different target analytes. Referring to FIGS. 6, 7A, 7B and 7C, one example set of dimensions is as follows:

angle $\theta 1 \sim 124°$,
angle $\theta 2 \sim 56°$,
angle $\theta 3 \sim 124°$,
width wd along center line $130 \sim 75$ micrometers,
length of first side $122 \sim 72$ micrometers,
length of second and seventh sides 123, $128 \sim 32.2$ micrometers,
length of third and sixth sides 124, $127 \sim 36$ micrometers,
length of fourth and fifth sides 125, $126 \sim 32.6$ micrometers,
height h of the three triangular pillar 110 (see FIG. 7B)~500 micrometers, and
flow channels fcw1 and fcw2 (see FIG. 7C)~10 micrometers.

Figure 8:
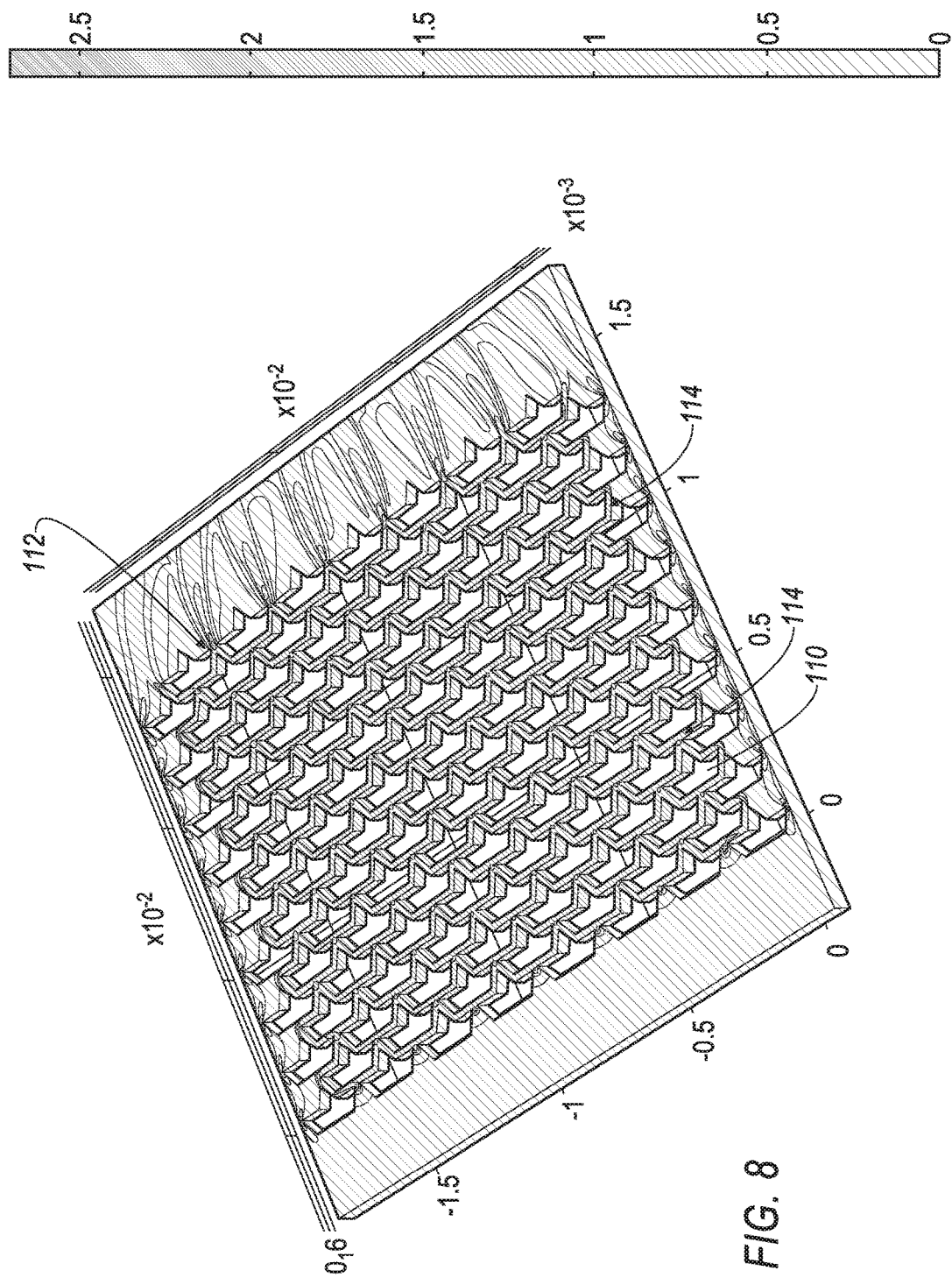
FIG. 8 illustrates example mobile phase flow rates through the separator structure.

FIG. 8 illustrates an example velocity profile of fluid through the separator structure 112 which demonstrates a slow passage enhancing the compound separation capability. The three-triangle pillar 110 increases separation and constant flow as compared to other microstructures.

Figure 9:
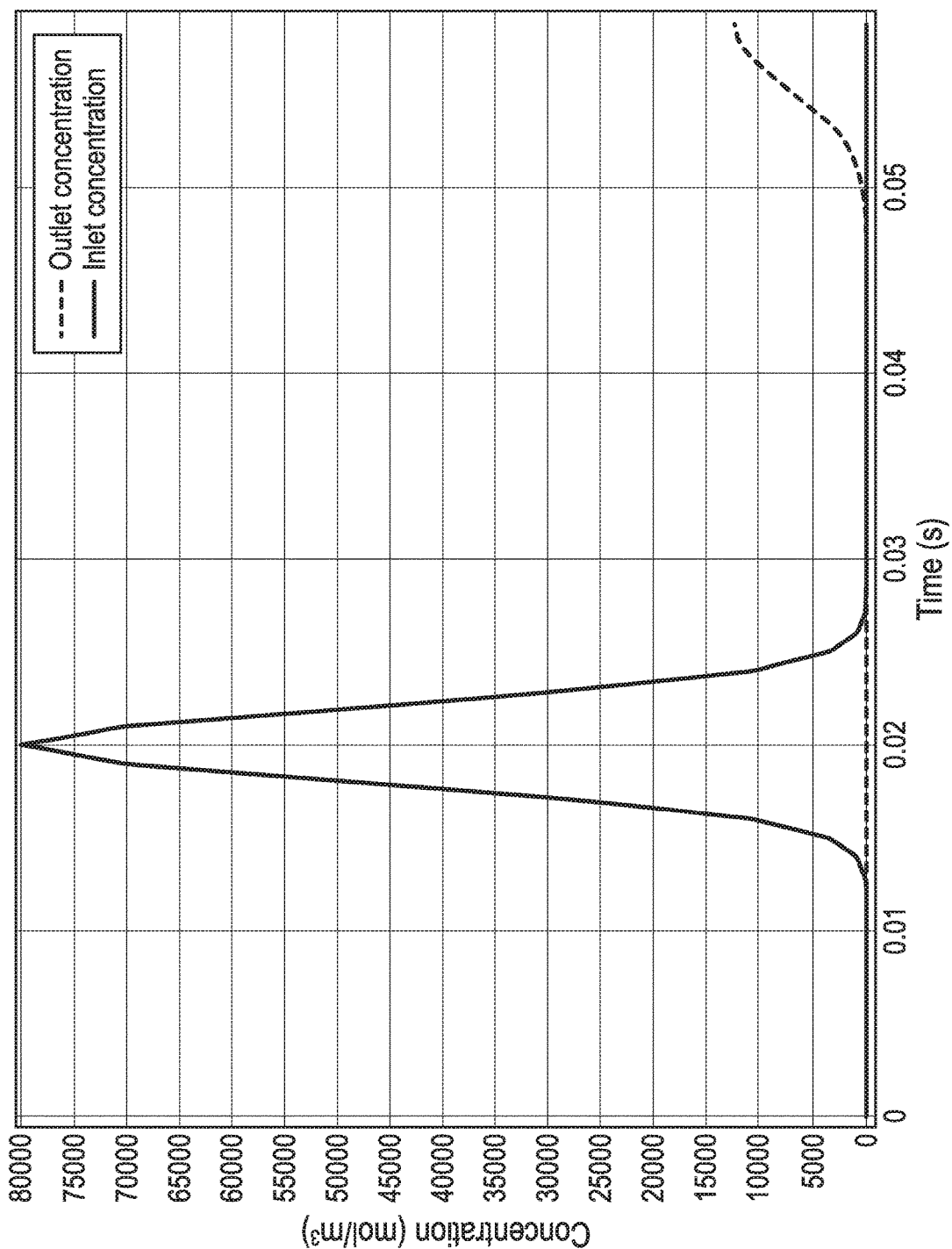
FIG. 9 illustrates an example flow separation of two constituents within the separator column.

FIG. 9 illustrates an example flow separation of two constituents with the separator column 86. The result indicates a wide separation and concentration of components due to the microfluidic structure of the three-triangular pillar 110.

Figure 10:
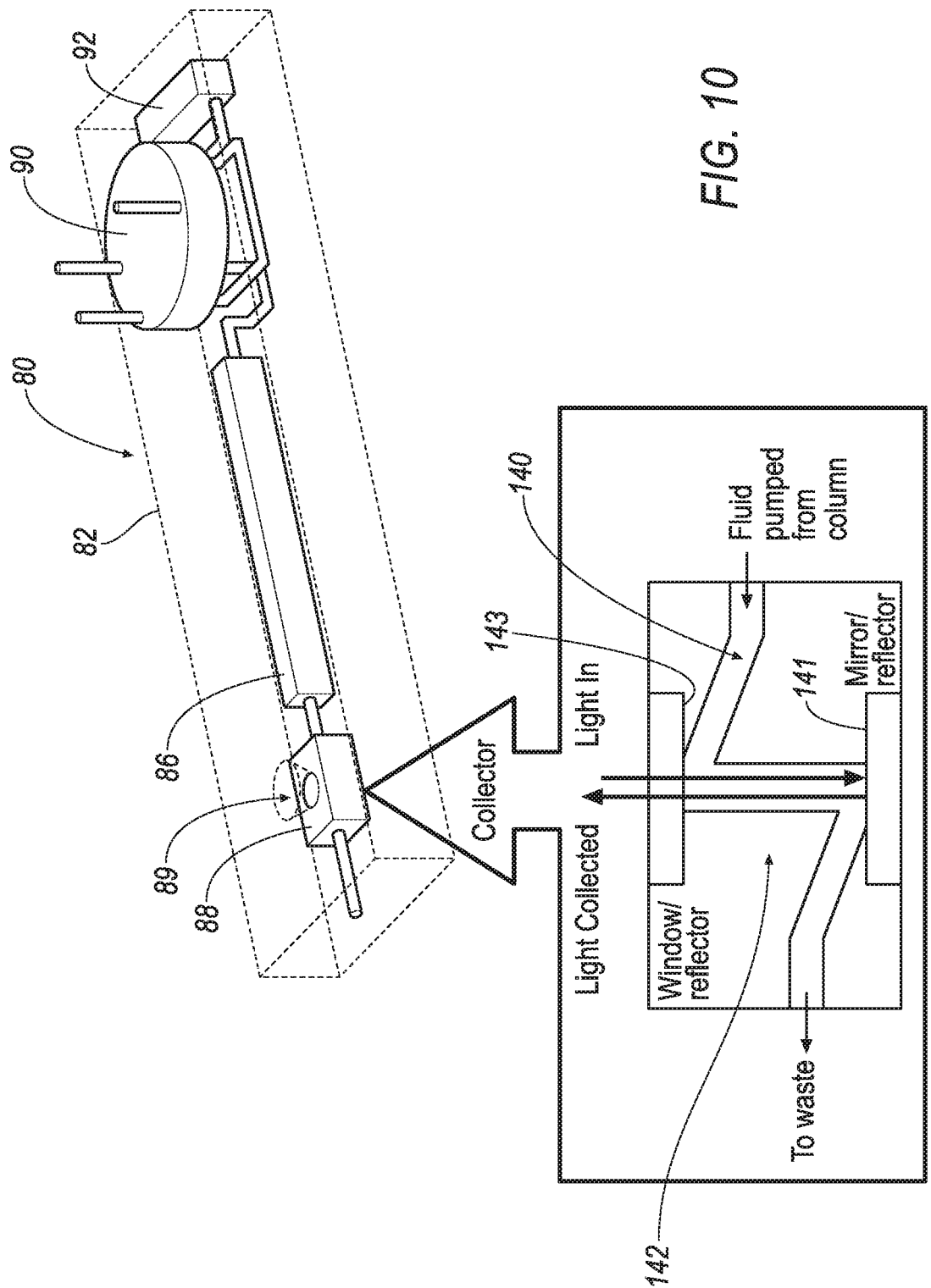
FIG. 10 illustrates an example liquid chromatography unit including a configuration for a collector.

With reference to FIG. 10, fluid that is pumped through the separator column 86 enters the collector 88 through a flow channel. The collector 88 of the chip 82 includes a second optically transparent window 89 on the top face of the chip 82 and continuing through to the collector 88 to permit spectral acquisition of an analyte as it elutes from the separator column 86 at its characteristic retention time. The chip 82 is arranged within the sample cartridge 70 such that the second optically transparent window 89 on the chip 82 aligns with the port 25 on a casing of the sample cartridge 70. The chip 82 in this example includes a mirror/reflector 141 and a window/reflector 143.

Light, typically from the laser 56 (see FIG. 1), is directed onto the sample and the scattered light collected with by the receiver 58 (FIG. 1). FIG. 10 shows a 180° backscattering geometry for light collection. The collected light is generally sent through a filter to remove or block light corresponding to the laser wavelength, allowing the Raman scattered light to be received and analyzed to obtain the Raman spectrum. Since each compound has a unique Raman spectral fingerprint, the signature serves as a means for identification.

A flow channel 140 in the collector 88 of the chip 82 may be a straight channel or have a z-shaped cross section 142 (when viewed from the side) to increase the measurement depth. A trade-off occurs between the amount of light signal that can be collected and the depth of field within the sample. As an example, optics with a large f/# collect light with a smaller solid angle than optics with a smaller f/# but have a larger depth of field and are less reliant on an accurate focus. The measurement depth and volume for Raman interrogation is optimized for the sample of interest in order to minimize Raman signals that may arise from the second optically transparent window 89 or flow channel material.

There are a number of techniques, based on the Raman Effect, that offer improved signal-to-noise ratio over conventional Raman spectroscopy. A few examples include, but are not limited to, total internal reflection spectroscopy (TIR) and surface enhance Raman spectroscopy (SERS), shown in FIG. 11. Total internal reflection (TIR) Raman spectroscopy is a surface-sensitive technique for obtaining spectroscopic information of a sample from a region within approximately 100-200 nm of a surface, FIG. 11, block labeled A:TIR. There are few basic requirements for TIR Raman scattering from a thin film at an interface. First, the first media 144, through which the laser beam is delivered, has a higher refractive index than the second media 146. Second, the angle $\phi 1$ of the laser beam traveling through first media 144 is incident on second media 146 is larger than a critical angle. The laser beam will be totally reflected at the interface with only and evanescent wave penetrating into second media 146. If the sample (second media 146) is transparent, Raman scattered light can be collected through the sample itself.

The block labelled B: SERS in FIG. 11 illustrates an example of surface enhanced Raman spectroscopy (SERS). SERS is a method to enhance the weak signals in spontaneous Raman spectroscopy that employs metallic nanostructures 150 on a nano-patterned substrate 151 capable of providing surface enhanced Raman scattering with potential enhancement factors of $\sim 10^5$ to $10^{10}$. There are three mechanisms of enhancement described in the literature: an electromagnetic effect, molecular resonance within the molecule, and charge transfer resonance between the molecule and substrate. The electromagnetic effect is dominant with signal enhancement resulting from the resonant interaction of light with plasmons excited at the surface of the structure. An enhanced electric field is created that is localized to a region of a few nanometers from the surface that subsequently can lead to an increase in the signal of Raman bands for molecules located in the vicinity of the metallic substrate. In the present example, metallic nanostructures 150 will be patterned in a flow channel 152 of the Raman acquisition zone to enable an array of features with homogeneous size, shape, controlled aspect ratio and feature spacing. One technique uses an Excimer laser to fabricate microbumps on a metallic thin film deposed in the flow channel 152 that will contact the analyte. An alternative method uses a nano-hot embossing technique to pattern the surface of the flow channel that is exposed to the analyte which in turn is coated with a metallic material. This technique will allow highly precise and reproducible wavelength tunable SERS substrates with feature sizes down to 25 nm to be fabricated. Traditionally, the lack of repeatability and uniformity of nano-spheres and structures create variability in the SERS spectra. This is uniquely overcome with the highly repeatable and ultra-high resolution of the nano-embossing system and the triangular pillar 110. Utilizing this method, the Raman signal of the analyte at the surface of the SERS substrate will be significantly enhanced to allow repeatable and quantifiable ultra-low concentration analysis.

Figure 12:
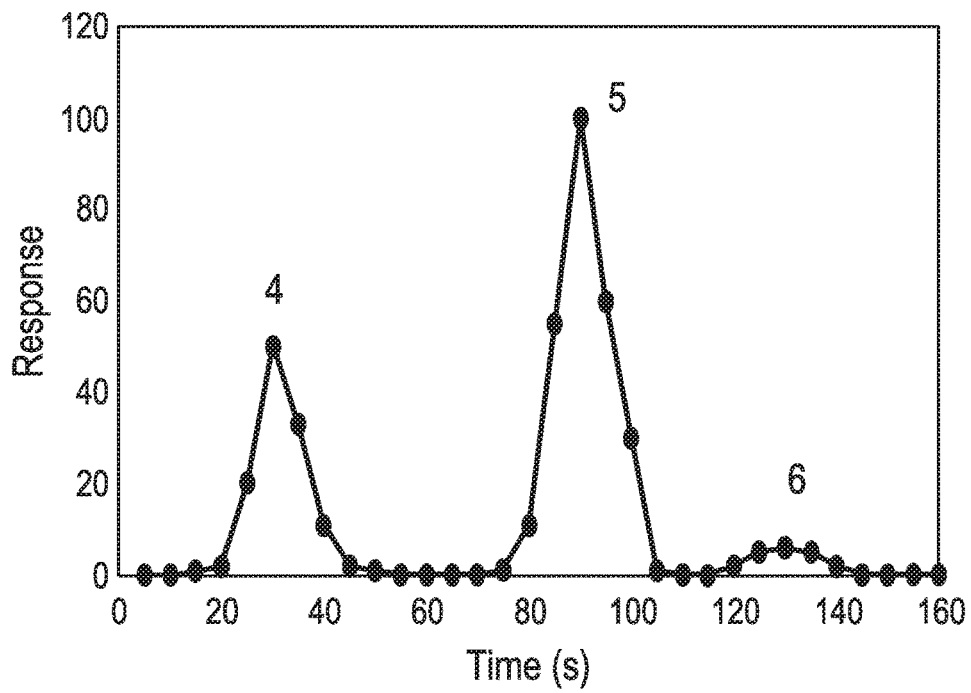
FIG. 12 illustrates an example separation of constituent components in time as a separated sample flows out of a separator column.
Figure 13:
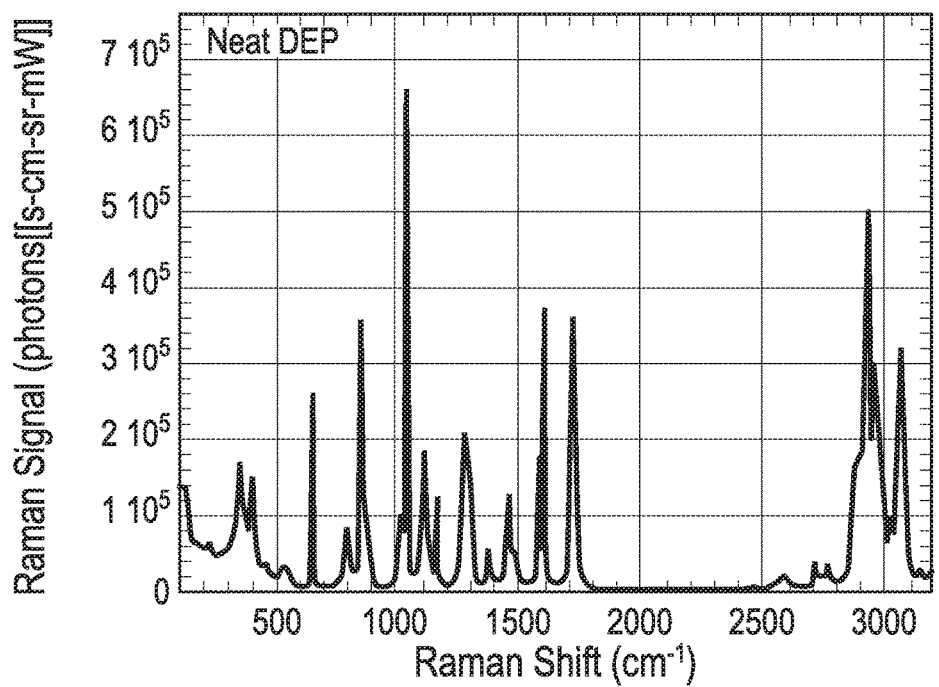
FIG. 13 illustrates an example of Raman data taken from the separated sample at a time.

FIGS. 12 and 13 relate to an approach for obtaining both qualitative and quantitative measurements of the analyte of interest. A sample injected into the sample cartridge 70 passes though the separator column 86 included in the chip 82. Physical separation is based on the differential migration of analytes in a mobile phase as they move along a stationary phase in the separator column 86, As the components flow out the separator column 86, Raman spectra will be taken at defined time intervals over the duration of the run as illustrated by the circles in a mock output concentration profile, FIG. 12. This example graph shows the concentration level of sample constituents at different time points as the separated constituents pass by the optical window.

Software algorithms will mine the Raman data taken as a function of time. Based on spectral features, spectra belonging to the same analyte will be grouped together and compared to a spectra library 31 for analyte identification. This is illustrated in FIG. 13. Once identified, the concentration of a particular analyte at each time point will be determined from which the total concentration calculated.

Figure 14:
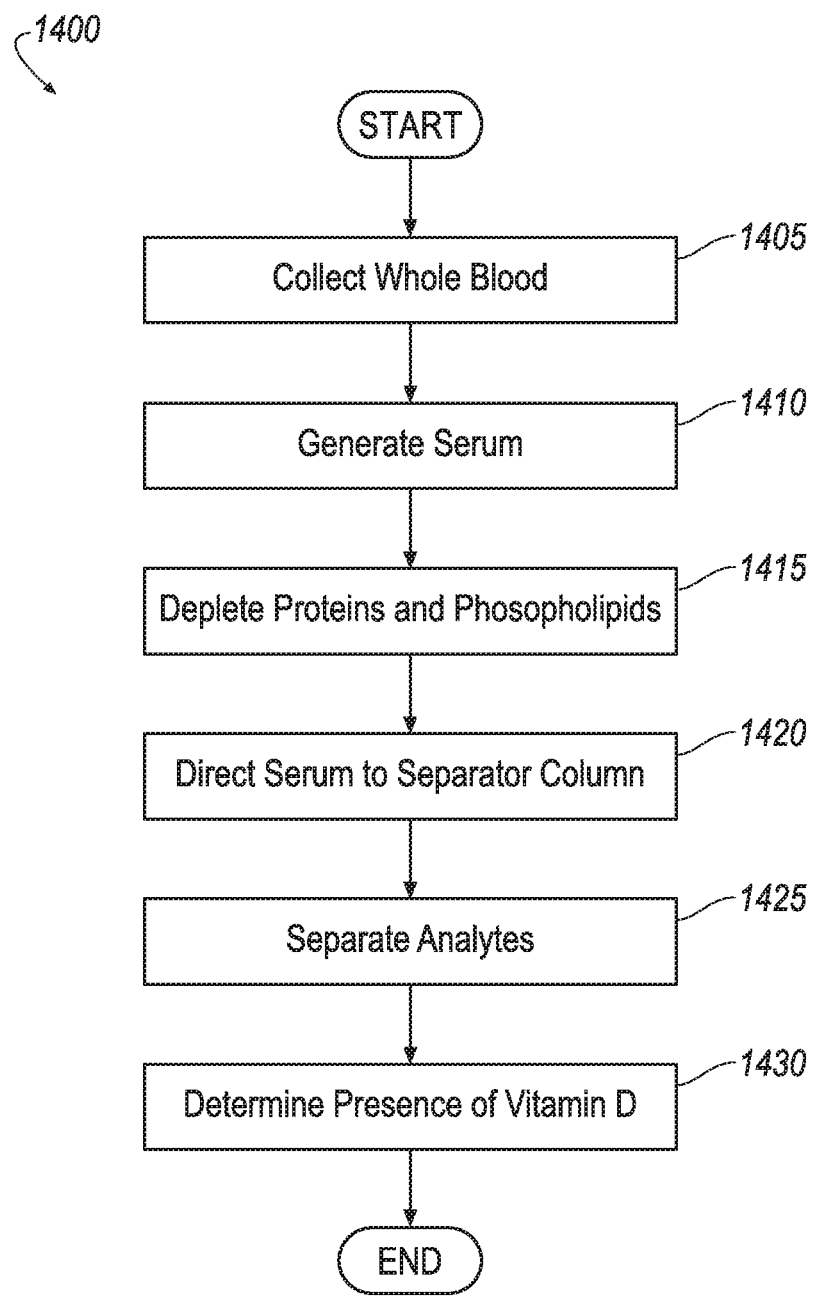
FIG. 14 is a diagram of an example process for determining the Vitamin D content in blood.

FIG. 14 is a diagram of an example process 1400 for determining the Vitamin D content of blood. The process 1400 starts in a block 1405.

In the block 1405, whole blood is collected from a patient using a syringe as is known. The process 1400 continues in a block 1410.

In the block 1410, serum is generated from the whole blood as is known. The process 1400 continues in a block 1415.

In the block 1415, the spectrometer 20 is operable to deplete proteins and phosopholipids from the serum. A sample cartridge 70 receives, for example from a user, a sample of the serum. The main body 22 of the spectrometer 20 receives the sample cartridge 70. For example, the sample cartridge 70 is inserted into the main body 22 by the user.

The computer 50 is programmed to operate the spectrometer 20 to deplete the proteins and phosopholipids from the serum. For example, the computer 50 may operate the pump to transport the sample through the valve 90 in the LC unit 26 of the sample cartridge 70 and into the sample pretreatment chamber 92 in the LC unit 26 of the sample cartridge 70. The sample pre-treatment chamber 92 may be arranged to deplete the proteins and phosopholipids from the serum. For example, the sample pre-treatment chamber 92 may include a first separator structure 112A such as the separator structure 112 described above. The first separator structure 112 may include three-triangular pillars 110 treated with, for example, protein or phospholipid binders, to remove the proteins and phosopholipids from the serum. The process 1400 continues in a block 1420.

In the block 1420, the computer 50 is programmed to pump the serum with the proteins and phosopholipids removed, into and through the separator column 86. For example, the computer 50 may reposition the valve 90 to direct the serum with the proteins and phosopholipids removed into the separator column 86. The separator column 86 may include a second separator structure 112B such as the separator structure 112 described above. The second separator structure 112B may include three-triangular pillars 110 treated to separate the Vitamin D and other analytes from the serum. This can include a reversed phase stationary phase (non-endcapped or endcapped), wherein the reversed phase stationary phase may be polymer-based or silica-based. Any reversed phase stationary phase may be used, such as Pentafluorophenyl (F5), C-1, C-4, C-8 and C-18. As an example, a reverse phase C-18 column utilizes ocadecylsilane bonded to a support material. The process continues in a block 1425.

In the block 1425, the serum, separated into analytes, may pass through the collector 88. As it passes through the collector 88, the spectrometer 20 may collect data such as Raman data from the serum. The computer 50 may be programmed to activate the laser 56 at specific times. The receiver 58 may receive back-scattered light from the serum and provide spectrum data to the computer 50. The process 1400 continues in a block 1430.

Figure 15:
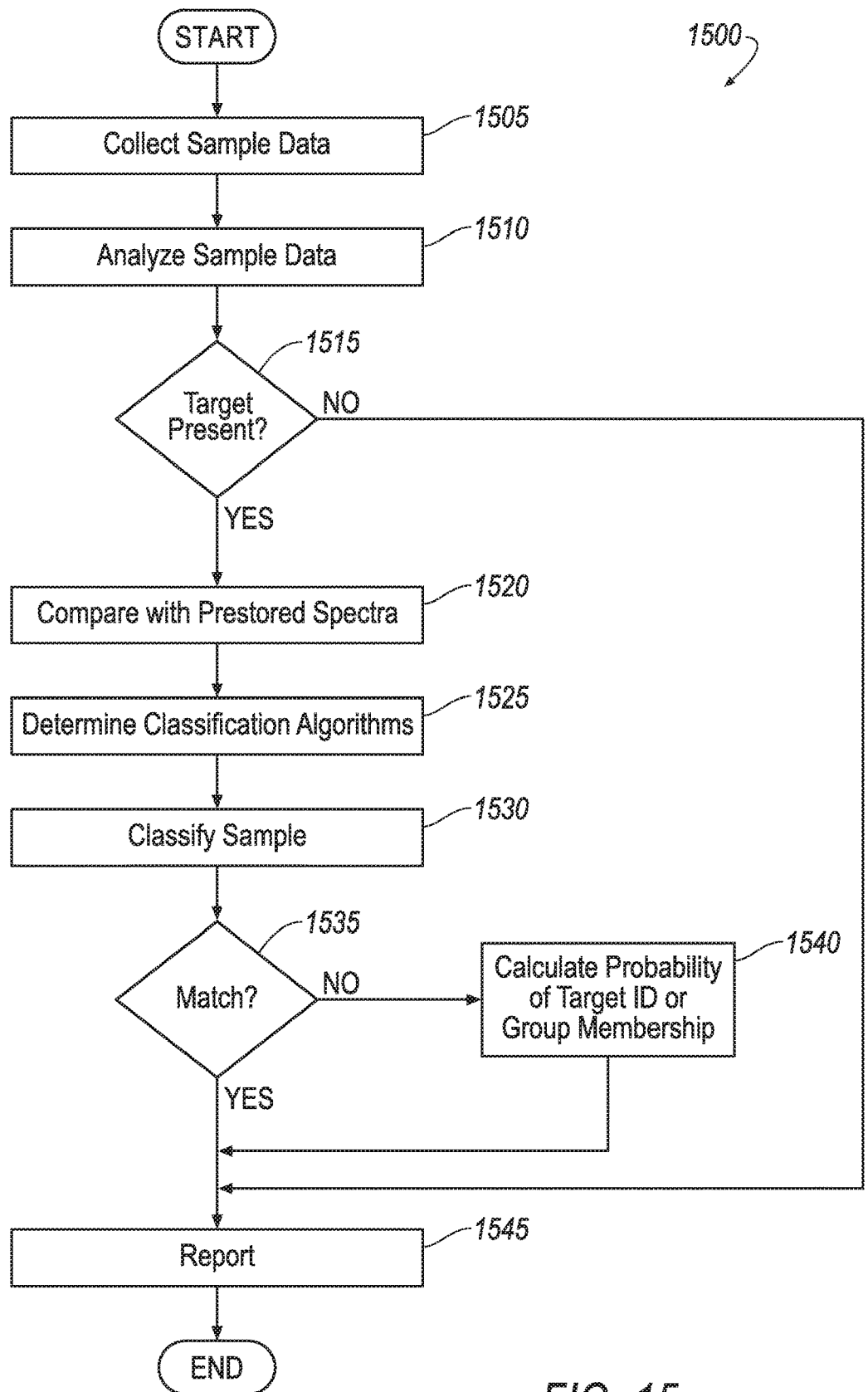
FIG. 15 is a diagram of an example process for analyzing Raman data to identify constituents of the separated sample.

In the block 1430, the computer 50 and/or server 30 may analyze the data as described with regard to FIG. 15 to determine the presence of target analytes. In this case, a target analyte is Vitamin D. The process 1400 ends.

FIG. 15 is a diagram of an example process 1500 for analyzing Raman data to identify constituents of the separated sample. The process 1500 starts in a block 1505.

In the block 1505, the spectrometer 20 collects data from a sample. As discussed above, a laser 56 in the main body 22 of the spectrometer 20 irradiates a sample in the sample cartridge 22 via the port 25. A receiver 58 in the main body 22 of the spectrometer 20 collects back-scattered light from the irradiated sample. The receiver 58 provides data representing a spectral composition of the back-scattered light to the computer 50 at different times, as the sample passes through the collector 88. The computer 50 may store the for further processing and/or transmit the data to the server 30 via the network 40 for processing. The data is stored with time stamps indicating when, during the data collection process, the data was received. The process 1500 continues in a block 1510.

In the block 1510, the computer 50 or server 30 analyze the data. The computer 50 or server 30 searches for spectral features in discrete Raman bands which may indicate the presence of a target. The discrete Raman bands will have time stamps corresponding to when the passed through the collector 88. The process 1500 continues in a block 1515.

In the block 1515, the computer 50 or server 30 determines whether target features are found indicating the likely presences of the target in the different Raman bands. In the case that target features are identified in a Raman band, the process 1500 continues in a block 1520. In the case that the target is likely not present in the sample (e.g., no target features are found), the process 1500 continues in a block 1545.

In the block 1520, the computer 50 or server 30 compares data samples determined in the block 1515 to include target features with prestored spectra. The prestored spectra may be taken from the spectra library 31. The process continues in a block 1525.

In the block 1525, the computer 50 or server 30 applies classification algorithms to the data The process 1500 continues in a block 1530.

In the block 1530, the computer 50 or server 30 performs typing via a hierarchical approach. Classification is assigned as one moves down the hierarchy. The process 1500 continues in a block 1535.

In the block 1535, the computer 50 or server 30 determines whether there is a match. in the case that there is a match, the process continues in a block 1545. In the case that there is not a match, the process 1500 continues in a block 1540.

In the block 1540, the computer determines the probability that a match was determined and/or the probability that an analyte belonging to a particular group was identified. The process 1500 then continues in a block 1545.

In the block 1545, the computer 50 or server 30 reports results of the measurement. The computer 50 or server 30 may provide data to a user via the user interface 52. Additionally or alternatively, the computer 50 or server 30 may provide a report to another computer, for example via the network 40.

The invention claimed is:

1. A sample cartridge for a liquid chromatography device comprising:
   a microfluidic chip;
   a collector formed in the microfluidic chip comprising a collector flow channel and a first window for acquisition of spectral data from a sample in the collector flow channel; and
   a separator column formed in the microfluidic chip including:
      a separator structure including a plurality of pillars arranged in stacked rows; and
      a separator flow channel including spaces between adjacent pillars, wherein:
         each pillar in the plurality of pillars includes seven sides and is symmetrical around a centerline;
         the seven sides include a first side, a second side, a third side, a fourth side, a fifth side, a sixth side and a seventh side;
         the first side is connected to the second side at a first end and connected to the seventh side at a second end, wherein the centerline extends perpendicularly from a middle of the first side;
         the second side and seventh side extend away from the first side in opposite directions, each forming an obtuse angle $\theta 1$ with the first side;
         the second side extends between the first side and the third side;
         the third side extends in a direction parallel to the first side and towards the centerline, forming an acute angle $\theta 2$ with the second side;
         the seventh side extends between the first side and connects to the sixth side;
         the sixth side extends in a direction parallel to the first side towards the centerline;
         the third side extends between the second side and the fourth side;
         the fourth side extends in a direction away from the first side and toward the centerline in a direction parallel to the seventh side, forming an angle $\theta 3$ with the third side;
         the sixth side extends from the seventh side to the fifth side;
         the fifth side extends in a direction away from the first side and toward the centerline in a direction parallel with the second side; and
         the fifth side and fourth side connect at an apex of the pillar, forming an angle $\theta 4$.

2. The sample cartridge of claim 1, wherein the pillars define the separator flow channel.

3. The sample cartridge of claim 2, wherein:
   in each row of pillars in the separator structure, a spacing from a center of one pillar to a center of an adjacent pillar is a distance w; and
   a subsequent row of pillars is laterally offset from a preceding row of pillars by a distance w/2.

4. The sample cartridge of claim 1, wherein the microfluidic chip further comprises a switching valve.

5. The sample cartridge of claim 4, wherein the switching valve is in fluid communication with the separator column in at least one position.

6. The sample cartridge of claim 1, wherein the collector comprises a reflector.

7. The sample cartridge of claim 1, wherein the collector comprises a nano-patterned substrate.

8. The sample cartridge of claim 1, further comprising:
   a case enclosing the sample cartridge, the case including a port aligned with the first window such that backscattered light from the sample can pass through the window and further through the port.

9. The sample cartridge of claim 8, wherein the case is configured to physically engage a Raman spectrometer.

10. A separator column formed in a microfluidic chip, the separator column comprising:
    a separator structure including a plurality of pillars arranged in stacked rows; and
    a separator flow channel including spaces between adjacent pillars, wherein:
       each pillar comprises seven sides and is symmetrical around a centerline;
       the seven sides include a first side, a second side, a third side, a fourth side, a fifth side, a sixth side and a seventh side;
       the first side is connected to the second side at a first end and connected to the seventh side at a second end, wherein the centerline extends perpendicularly from a middle of the first side;
       the second side and seventh side extend away from the first side in opposite directions, each forming an obtuse angle $\theta 1$ with the first side;
       the second side extends between the first side and the third side;
       the third side extends in a direction parallel to the first side and towards the centerline, forming an acute angle $\theta 2$ with the second side;
       the seventh side extends between the first side and connects to the sixth side;
       the sixth side extends in a direction parallel to the first side towards the centerline;
       the third side extends between the second side and the fourth side;
       the fourth side extends in a direction away from the first side and toward the centerline in a direction parallel to the seventh side, forming an angle $\theta 3$ with the third side;
       the sixth side extends from the seventh side to the fifth side;
       the fifth side extends in a direction away from the first side and toward the centerline in a direction parallel with the second side; and
    the fifth side and fourth side connect at an apex of the pillar, forming an angle $\theta 4$.

11. The separator column of claim 10, wherein:
    in each row of pillars in the separator structure, a spacing from a center of one pillar to an adjacent pillar is a distance w; and
    each row of pillars is laterally offset from a preceding row of pillars by a distance w/2.

12. The separator column of claim 10, wherein the plurality of pillars are formed on a substrate and extend above the substrate.

13. The separator column of claim 12, further comprising a top plate connected to a top side of the separator structure and forming a top of the separator flow channel.

14. The separator column of claim 10, wherein a width of the pillar from the first side to the apex along the centerline is in a range from five micrometers to 100 millimeters.

15. The separator column of claim 10, wherein:
 angle $\theta 1$ is in a range from 95° to 155°;
 angle $\theta 2$ is 180° minus angle $\theta 1$; and
 angle $\theta 3$ is substantially equal to angle $\theta 1$.

16. The separator column of claim 10, wherein a width of the separator flow channel between two adjacent pillars is in a range from one micrometer to 100 micrometers.

\* \* \* \* \*